United States Statutory Invention Registration [19]

[11] Reg. Number: H150

Hankner et al. [43] Published: Nov. 4, 1986

[54] ACCESSORY MODULE FOR IMPLANTABLE FLUID DISPENSING DEVICE

[75] Inventors: Douglas O. Hankner, Moundsview; Larry A. Lundeen, Blaine, both of Minn.

[73] Assignee: Medtronic, Inc., Minneapolis, Minn.

[21] Appl. No.: 637,353

[22] Filed: Aug. 3, 1984

[51] Int. Cl.[4] ..... A61M 5/00
[52] U.S. Cl. ..... 604/93; 604/892
[58] Field of Search ..... 604/93, 131, 167, 891, 604/892, 181-182, 151

[56] References Cited

U.S. PATENT DOCUMENTS

| | | | |
|---|---|---|---|
| 4,146,029 | 3/1979 | Ellinwood | 128/260 |
| 4,193,397 | 3/1980 | Tucker et al. | 604/131 |
| 4,310,001 | 1/1982 | Comben | 604/891 |
| 4,360,019 | 11/1982 | Portner et al. | 604/892 |
| 4,447,234 | 5/1984 | Mayfield | 604/152 |
| 4,487,603 | 12/1984 | Harris | 604/152 |

*Primary Examiner*—Deborah L. Kyle

*Assistant Examiner*—Michael J. Carone

*Attorney, Agent, or Firm*—John L. Rooney; Joseph F. Breimayer

[57] ABSTRACT

An implantable fluid dispensing device has an accessory housing set into the biocompatible shape of its device canister. A shelf is set into the canister to accept the accessory housing which contains a filter, an externally accessible infusion septum, or other accessory. The function of accessories in the accessory housing is independently tested. After an accessory is selected to match the particular application, the accessory module is mounted on the canister.

13 Claims, 10 Drawing Figures

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

Fig.4
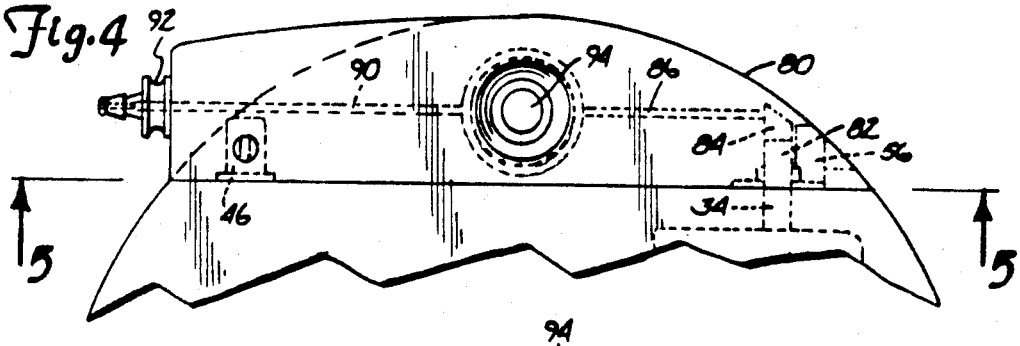
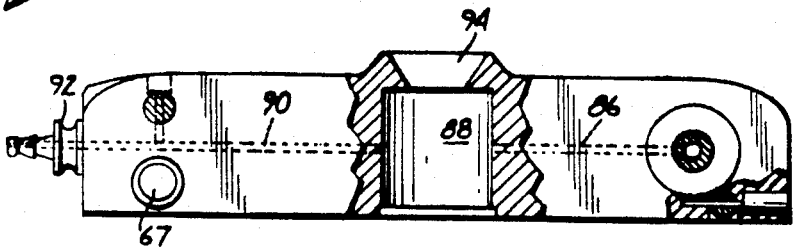
Fig.5
Fig.6
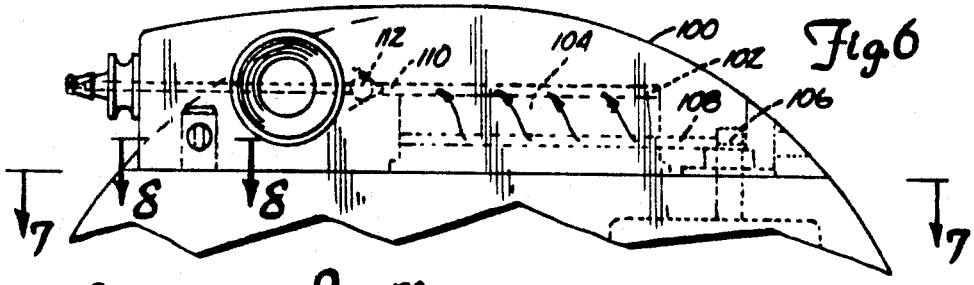
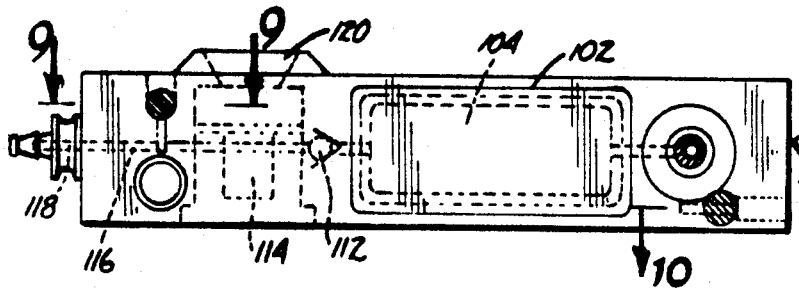
Fig.7
Fig.9
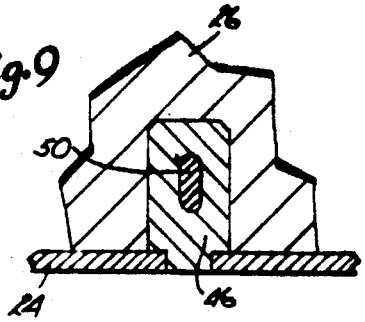
Fig.10
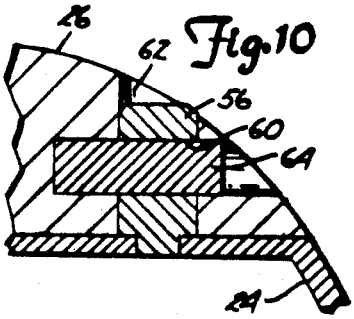
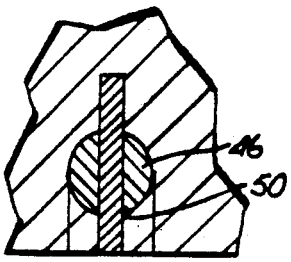
Fig.8

ACCESSORY MODULE FOR IMPLANTABLE FLUID DISPENSING DEVICE

BACKGROUND OF THE INVENTION

1. Field of the Invention

The present invention relates to accessory modules designed for mounting on implantable fluid dispensing devices.

2. Background Art

A variety of fluid dispensing devices have attempted to more carefully regulate diseases or pain in patients by delivering drugs to particular sites within the body. For example, it is believed that insulin delivery by an implantable dispenser will regulate diabetes in a manner impossible through traditional injections.

These devices must be sealed to prevent migration of fluids between the patient's body and the interior of the device. The common technique has been to weld shut a metallic container, using technology similar to that in heart pacemakers. This method of sealing a case is effective, but is permanent and expensive to alter. Components within the case must be considered permanently encapsulated.

Particular applications of such fluid dispensing devices could be enhanced by having various accessories in combination with the permanent parts of the device, which reside within the case. For example, some drug therapies are safer if the drug is filtered for either particles or bacteria. Because each drug and therapy has specific characteristics, it is expensive and impractical to design a variety of such filters as part of the permanent apparatus sealed within the case.

Another example of an accessory for the module is a port for infusion of drugs on an acute basis, to supplement the chronic administration provided by the fluid dispensing device. Attempts have been made to add external ports to be used in conjunction with such devices. For example, see the port disclosed in U.S. Pat. No. 4,360,031 to White, issued Nov. 23, 1982. An external port is disclosed in U.S. Pat. No. 3,971,376 to Wichterle issued July 27, 1976.

A means is needed to accommodate such drug-specific and application-specific devices other than permanently mounting them within the sealed case. Great manufacturing expense can be saved if accessory devices can be added after the original manufacture. Better medical flexibility could be achieved if doctors could specify particular accessories to be added after manufacture.

SUMMARY OF THE INVENTION

The present invention provides an accessory module for mounting accessories on an implantable fluid dispenser. A metallic case is sealed permanently to include a fluid reservoir, means for pumping the fluid, and outlet means to pass fluid to the exterior of the case. The case has a smooth biocompatible shape. It is generally curved to avoid irritation within the body. An indentation or shelf is set into this curved surface.

An accessory module, preferably of a biocompatible non-metallic material, is shaped to fit in the indentation or shelf so that, when it is in place, an accessory housing of the module completes the curve of the case and presents to the patient a smooth complete curved surface, which does not cause irritation.

The accessory housing has a fluid inlet means for coupling to the fluid outlet means on the case. It also has an accessory fluid outlet means to pass fluid from the accessory housing out to the body of the patient through an attached catheter.

In one embodiment, the accessory housing includes a filter for filtering fluid as it passes from the accessory inlet to the accessory outlet.

In another embodiment, the accessory housing includes a port to allow fluid to be directed into the accessory housing and into the attached catheter from outside the patient's body. In one example, the port is a septum for receiving a hypodermic needle. This allows direct injection from outside the body of the patient of fluid which would pass through the housing outlet into a catheter into the patient's body without interfacing with the sealed case.

A fluid dispensing device constructed according to the present invention allows great savings of manufacture in that various accessories can be added to the device after its manufacture. A doctor can specify a particular type of filter, or a particular type of port, or other accessory to be added on to a fluid dispensing device after its manufacture. In one embodiment, such devices can be added by the doctor at the site of implantation.

By separating accessories from the sealed case, the accessories can be separately tested. Testing filters, for example, within a sealed fluid dispensing device is extremely difficult. Filters can be separately tested in the present invention and later added for use in the patient.

This invention solves the prior art problems of bulky or loose devices added to the fluid dispensing device. The device retains the same smooth body-compatible curve to minimize irritation to tissue of the patient. The accessory devices are fixedly mounted on the sealed case in a location where they may be easily located by the physician. The greatest possible flexibility in combinations of accessory devices and economy is achieved.

BRIEF DESCRIPTION OF THE DRAWINGS

FIG. 4 is a fragmentary enlarged view of a second embodiment of the accessory module of FIG. 1;

FIG. 5 is a partially cross-sectional, partially cut-away view taken on line 5—5 of FIG. 4;

FIG. 6 is an enlarged fragmentary view of a third embodiment of the accessory module of FIG. 1;

FIG. 7 is a partially cross-sectional, partially cut-away view taken on line 7—7 of FIG. 6;

FIG. 8 is an enlarged fragmentary cross-sectional view taken on line 8—8 of FIG. 6;

FIG. 9 is an enlarged fragmentary cross-sectional view taken on line 9—9 of FIG. 7; and FIG. 10 is an enlarged fragmentary cross-sectional view taken on line 10—10 of FIG. 7.

DETAILED DESCRIPTION OF THE PREFERRED EMBODIMENT

Figure 1:
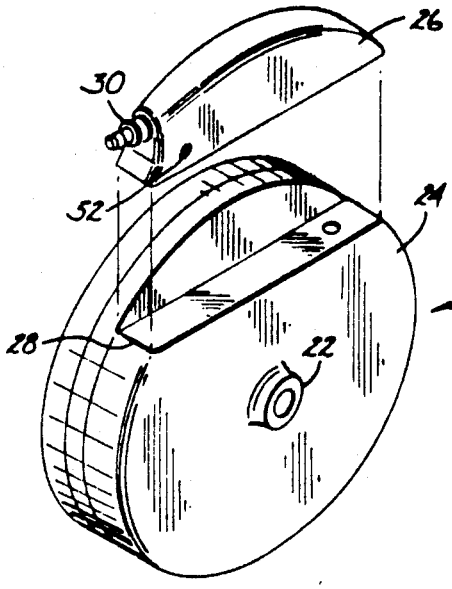
FIG. 1 is a perspective view of a fluid dispensing device with an accessory module mounted.

An implantable drug dispenser 20 is illustrated having a smooth exterior surface which minimizes irritation on human tissue when implanted. The particular dispenser 20 illustrated is shaped like a short cylinder, similar to a hockey puck with rounded edges. Drug dispenser 20 is provided with an inlet 22 for filling with a selected medication. In the example illustrated, inlet 22 is a septum which is pierced with a hypodermic needle inserted through the patient's skin.

Drug dispenser 20 includes a sealed canister 24 and an accessory housing 26. Canister 24 is preferably made of a biocompatible metal, such as titanium, which is welded to make a hermetically sealed enclosure for the fluid reservoir and mechanics of the drug dispenser 20. Canister 24 is provided with an indentation 28 which is set in from the normally smooth shape of canister 24. In this case, indentation 28 is a shelf. In other embodiments, indentation 28 is a section removed from the shape of canister 24. Accessory housing 26 is shaped to mount in shelf 28, so that it blends into the smooth biocompatible outside curve of canister 24.

Accessory housing 26 1s preferably made of biocompatible, drug-compatible material, such as an inert plastic like polypropylene.

An accessory fluid outlet 30 is mounted on accessory housing 26. A fluid-conveying catheter is mounted on accessory fluid outlet 30 at the time of implantation.

In FIG. 1, accessory housing 26 is shown exploded away.

Figure 2:
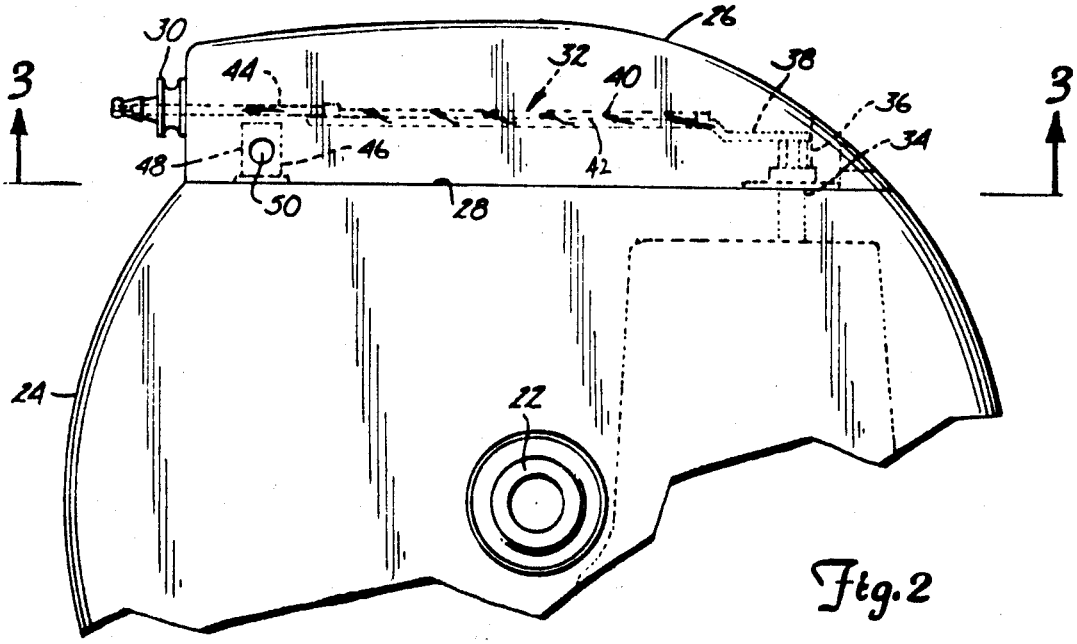
FIG. 2 is an enlarged fragmentary side elevational view of one embodiment of a first embodiment of the accessory module of FIG. 1.

The enlarged fragmentary view of FIG. 2 shows a first embodiment of the accessory module of FIG. 1 which includes a filter 32. Canister 24 includes a fluid outlet 34 which mates with an accessory fluid inlet 36 in accessory housing 26. Fluid passes out of a dispensing mechanism in canister 24 through canister fluid outlet 34, accessory fluid inlet 36 and passage 38 into a filter chamber 40 in accessory housing 26. In the embodiment illustrated, filter chamber 40 is a generally rectangular opening. A filter membrane 42 is mounted within filter chamber 40.

In one embodiment of this embodiment, the filter membrane is a hydrophyllic 0.1 micron pore-size bacterial/pyrogen retentive membrane. This membrane is constructed of an inert polymer such as nylon or PVDF to ensure long-term stability. In another embodiment, this filter membrane is a 50 micron pore-size membrane designed to filter larger particles and emboli. In another version of this embodiment, the filter membrane is partially hydrophyllic and partially hydrophobic to allow both drug and small gas bubbles to be filtered and to prevent any air lock.

In the embodiment illustrated, filter membrane 42 is rectangular. It extends across the entire filter chamber 40 so that fluid entering through passage 38 passes along one entire side of filter membrane 42 and must pass through membrane 42 to progress to passage 44, from where it passes out of accessory flu1d outlet 30. In this manner, all drug dispensed by fluid dispenser 20 is filtered by filter membrane 42 before being dispensed in the body of the patient.

Accessory housing 26 is mounted on canister shelf 28. A first mounting stud 46 on canister 24, protrudes into a first mounting hole 48 in accessory housing 26.

First mounting stud 46 is provided with a fixation slot 50 therethrough. A fixation access opening 52 is provided in accessory housing 26 which is open to first fixation slot 50. Once accessory housing 26 is positioned on shelf 28 so that first mounting hole 48 accepts first mounting stud 46, a fixation wedge 54 is inserted through first opening 52 into first fixation slot 50, thereby locking accessory housing 26 in place. In the illustrated embodiment, first opening 52 is then filled with plastic or adhesive material to hold first fixation wedge 54 in place.

Similarly, at an opposite end of accessory housing 26, a second mounting stud 56 on canister 24 is covered by a second mounting hole 58 in accessory housing 26. Second mounting stud 56 has a second fixation slot 60 therethrough. A second opening 62 in accessory housing 26 allows access from outside the accessory housing 26 to second fixation slot 60. A second fixation wedge 64 is inserted through second opening 62 into second fixation slot 60 to lock canister 26 to second mounting stud 56.

Accessory housing 26 is provided with an additional filling inlet opening 66. In the embodiment illustrated, the device 20 is pressurized with a constant pressure fluid through filling inlet 67. After the device is filled through inlet 67, the inlet 67 is permanently sealed. The inlet 67 projects slightly outside the canister 24. This inlet is accepted into inlet opening 66 as canister shelf 28 receives accessory housing 26.

The illustrated accessory housing is easily applied to canister 24 at any point after manufacture. The filter in the embodiment illustrated in FIG. 2 can be installed in the plastic housing 26 and fully tested without interacting in any way with the mechanisms in canister 24. When the time for final assembly arrives, whether it be at the factory or in a hospital setting, a housing 26 containing the appropriate filter membrane 42 is selected and mounted on first and second mounting pins 46 and 56.

Figure 3:
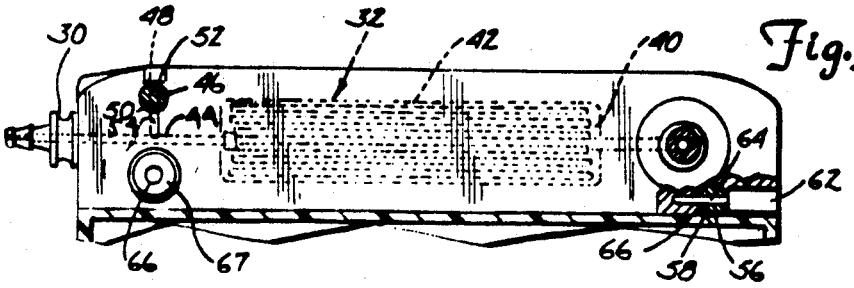
FIG. 3 is a partially cross-sectional view, partially cut-away view taken on line 3—3 of FIG. 2.

A second embodiment of an accessory housing is illustrated in FIGS. 4 and 5. Accessory housing 80 mounts on first and second mounting pins 46 and 56 in a manner identical to the embodiment illustrated in FIGS. 2 and 3. In this embodiment, accessory fluid inlet 82 includes a check valve 84 to prevent back-flow of fluid from accessory housing 80 into canister fluid outlet 34. Fluid received through accessory fluid inlet 82 passes through first passage 86 into a septum chamber 88 located in accessory housing 80. From septum chamber 88, fluid passes through second passage 90 and out through accessory fluid outlet 92 into the patient. Septum chamber 88 is accessible from outside of accessory housing 26 through piercible septum 94. This septum 94 operates in a manner similar to inlet 22 in canister 24. A hypodermic needle from outside the patient is inserted through the skin and through septum 94 into chamber 88. Fluid is then injected into chamber 88. Check valve 84 prevents back flow into canister 24. This fluid immediately passes through second passage 90 and out accessory outlet 92.

In this manner, acute dosages of drug or diagnostic fluids are injected into the patient without employing the pumping apparatus of canister 24. The accessory housing 80 is fixedly mounted on canister 24 and provides a smooth contour continuing the lines of canister 24. This fits well within the patient and prevents aggravation of surrounding tissue, yet provides additional acute drug access through septum 94. The prior art techniques of sharp or irregular projections from the device are avoided.

A third embodiment of the present invention is illustrated in FIGS. 6 and 7. This embodiment includes an accessory housing 100 provided with a filter chamber 102 and filter member 104 which operate in the manner of the embodiment illustrated in FIG. 2. Fluid is accepted through accessory fluid inlet 106, passes through first passage 108 and into filter chamber 102. After fluid passes through filter membrane 104 it proceeds through second passage 110. In second passage 110 is a check valve 112, shown in schematic form, which allows fluid to pass only in one direction. Second passage 110 opens into septum chamber 114. Chamber 114 is subsequently open to third passage 116 which empties into accessory outlet 118.

As in the embodiment illustrated in FIGS. 4 and 5, a septum 120 allows access by a hypodermic needle to septum chamber 114. Acute infusions of fluid may be injected by a hypodermic needle into chamber 114 as in the earlier described embodiments. Check valve 112 prevents the acute infusion of fluid from proceeding backward into filter chamber 102 or canister 24.

In this embodiment, accessory housing 100 mounts on shelf 24 in a manner identical to earlier illustrated embodiments.

With the present invention, various combinations of external accessories can be easily added to an infusion device to tailor the device to the need of the particular patient. As illustrated, a filter, an infusion septum, combination thereof, or other accessory can be installed in this manner without requiring complex factory installation. The preferred embodiment of accessory module can easily be fabricated, such as by molding, from a biocompatible polymer such as polypropylene or a fluoropolymer at little expense. The accessories in the accessory housing can be independently tested without interfacing with the complexities of the apparatus within the infusion pump canister. If there are failures in tested devices, they can be discarded at low cost without involving the great expense of scrapping or repairing the sealed case.

The correct accessory for the type of drug to be adminstered is selected and mounted on the canister as needed. In some preferred embodiments, the accessory housing is mounted by the physician after selection of the proper accessories. Specific filters can be stocked for specific drugs or therapies. This increases the likelihood that the proper device will be available in a timely manner when needed by a patient for whom has been prescribed a particular therapy. The choice can be made for each patient whether to include a filter, an infusion port, or a combination of accessories. This greatly increases the flexibility of the device, in that the doctor can alter characteristics of the device by choosing proper accessories designed to maximize treatment for the patient.

When new drug therapies are discovered which require different accessories, the accessories can be manufactured and tested without expensive redesign of components within the hermetically sealed case.

While the present invention has been illustrated in terms of particular embodiments, it should be noted that the invention may take the form of other useful embodiments not illustrated herein.

What is claimed is:

1. An implantable fluid dispensing device comprising:

a sealed case having a smooth biocompatible curved surface;

the case having an indentation inwardly diverging from the curved surface; and an accessory housing shaped to mount on the case in the indentation and shaped to conform generally to the curved surface.

2. The device of claim 1 further comprising:

fluid outlet means in the case for passing fluid from inside the case to outside the case;

fluid inlet means in the accessory housing for coupling to the fluid outlet means on the case when the housing is mounted on the case; and second fluid outlet means on the accessory housing for passing fluid from within the accessory housing into a patient's body.

3. The device of claim 2 further comprising filter means mounted in the accessory housing for filtering the fluid as it passes from the inlet means to the second outlet means.

4. The device of claim 2 further comprising:

port means on the accessory housing for receiving fluid to be passed through the accessory housing and out the second outlet means.

5. The device of claim 4 wherein the port means includes a pierceable septum for receiving fluid from a hypodermic needle inserted through skin of the patient.

6. An implantable fluid dispensing device comprising:

a sealed case having a fluid storage reservoir;

fluid outlet means on the case for passing fluid from the reservoir to the exterior of the case;

the case having a curved shape and having a shelf stepped in from the curved shape;

an accessory housing shaped to mount in the shelf and to conform generally to the external curved surface;

accessory fluid inlet means in the accessory housing for coupling to the fluid outlet means on the case and for passing fluid into the accessory housing;

filter outlet means in the accessory housing for passing fluid from the accessory housing into a patient's body; and filter means mounted in the accessory housing for filtering fluid passing from the accessory fluid inlet to the accessory fluid outlet.

7. The device of claim 6 further comprising an inlet port in the accessory housing for receiving fluid from outside the patient's body.

8. The device of claim 7 wherein the inlet port includes a septum for receiving a hypodermic needle.

9. An implantable fluid dispensing device comprising:

a sealed case having a fluid storage reservoir;

fluid outlet means on the case for passing fluid from the reservoir to the exterior of the case;

the case being shaped with a biocompatible curved perimeter and having a shelf stepped in from the curved perimeter;

an accessory housing mounted on the shelf and shaped to conform to the curved perimeter;

an inlet port mounted on the accessory housing for injecting fluid into the housing; and valve means for preventing fluid from the housing from passing into the sealed case.

10. The device of claim 9 further comprising filter means mounted in the accessory housing for filtering fluid as it passes through the accessory housing.

11. An accessory module for mounting on an implantable fluid dispensing device comprising:

an accessory housing formed of inert biocompatible plastic having one curved side shaped to contact the interior of the body in a non-irritating manner and a second side shaped to be inset in its fluid dispensing case;

accessory fluid inlet means mounted on the accessory housing for receiving fluid;

accessory outlet means mounted on the housing for dispensing fluid; and an accessory mounted within the housing for processing fluid.

12. The device of claim 11 wherein the accessory is a filter for filtering fluid as it passes through the housing.

13. The device of claim 11 wherein the accessory is a port for receiving fluid from a source external to a patient's body and a valve for preventing flow of fluid out of the accessory inlet port.

* * * * *